United States Patent [19]

Ni et al.

[11] Patent Number: 5,968,797
[45] Date of Patent: *Oct. 19, 1999

[54] UBIQUITIN CONJUGATING ENZYMES 8 AND 9

[75] Inventors: Jian Ni, Gaithersburg; Reiner Gentz, Silver Spring; Mark D. Adams, North Potomac, all of Md.

[73] Assignee: Human Genome Sciences, Inc., Rockville, Md.

[*] Notice: This patent is subject to a terminal disclaimer.

[21] Appl. No.: 08/903,396

[22] Filed: Jul. 22, 1997

Related U.S. Application Data

[60] Division of application No. 08/464,342, Jun. 5, 1995, Pat. No. 5,650,313, which is a continuation-in-part of application No. PCT/US95/01250, Jan. 31, 1995, abandoned.

[51] Int. Cl.⁶ .............................. C12N 9/10; C12N 15/00; C07H 21/04
[52] U.S. Cl. ...................... 435/193; 435/440; 530/387.1; 536/23.2; 536/23.4
[58] Field of Search ..................... 435/193, 440; 536/23.2, 23.4; 530/387.1

[56] References Cited

U.S. PATENT DOCUMENTS

| | | | |
|---|---|---|---|
| 5,384,255 | 1/1995 | Ciechanover et al. | 435/193 |
| 5,565,352 | 10/1996 | Hochstrasser | 435/240.1 |
| 5,744,343 | 4/1998 | Draetta et al. | 435/193 |

FOREIGN PATENT DOCUMENTS

| | | |
|---|---|---|
| 95/18974 | 7/1995 | WIPO . |
| 95/27066 | 10/1995 | WIPO . |

OTHER PUBLICATIONS

Treier et al., Cell 78: 787–798 (1994).
Scheffner et al., Proc. Natl. Acad. Sci. 91: 8797–8801 (1994).
Kaiser et al., J. Biol. Chem. 269: 8797–8802 (1994).
Plon et al., Proc. Natl. Acad. Sci. 90: 10484–10488 (1993).
Dameron et al., Science, vol. 265: 1582–1584 (1994).
Hingamp et al., EMBO J. 11(1): 361–366 (1992).
Treier et al., EMBO J. 11 (1):367–372 (1992).
Wing et al., Biochem. 305 (1): 125–132 (1995).
Jentsch et al., TIBS 15: 195–198 (1990).
Silver et al., EMBO J. 11:3091–3098 (1992) abstract only.
Schneider et al., EMBO J. 9:1431–1435 (1990) abstract only.
Liu et al., J. Biol. Chem. 267:15829–15835 (1992) abstract only.
Rolfe et al., Proc. Natl. Acad. Sci 92: 3264–3268 (1995).
Robinson et al., Mammalian Genome 6: 725–731 (1995).
Ciechanover et al., Cell 79: 13–21 (1994).
Genbank Accession No. T19052 (Sequence and Annotations) Jun. 20, 1994.
Genbank Accession No. S81004 (Sequence and Annotations) Aug. 12, 1996.

*Primary Examiner*—Lisa Hobbs
*Attorney, Agent, or Firm*—Michele M. Wales

[57] ABSTRACT

Human UCE 7, UCE 8 and UCE 9 polypeptides and DNA (RNA) encoding such polypeptides and a procedure for producing such polypeptides by recombinant techniques is disclosed. Also disclosed are methods of utilizing such polypeptide for the treatment of the proliferation of malignant cells. Antagonists against such polypeptides and their uses as a therapeutic to treat Alzheimer's disease, atrophying skeletal muscle, African swine fever virus and apoptotic cell death are also disclosed. Also disclosed are diagnostic assays for detecting diseases related to mutations in UCE 7, 8 and 9 nucleic acid sequences and the concentration of polypeptides encoded by such sequences.

66 Claims, 9 Drawing Sheets

FIG. 1A

```
1    ATG GCT CTG AAG AGA ATC CAC AAG GAA TTG AAT GAT CTG
     M   A   L   K   R   I   H   K   E   L   N   D   L

76   GTT GGA GAT GAT ATG TTC CAT TGG CAA GCT ACA ATA ATG
     V   G   D   D   M   F   H   W   Q   A   T   I   M

151  TTC TTG ACA ATT CAT TTC CCA ACA GAT TAC CTC TTC AAA
     F   L   T   I   H   F   P   T   D   Y   L   F   K

226  CCA AAT ATT AAC AGT AAT GGC AGC ATG TGT CTT GAT ATT
     P   N   I   N   S   N   G   S   M   C   L   D   I

301  AAA GTA CTC TTG TCC ATC TGT TCT CTG TTG TGT GAT CCC
     K   V   L   L   S   I   C   S   L   L   C   D   P

376  ATC TAC AAA ACA GAT AGA GAA AAG TAC AAC AGA ATA GCT
     I   Y   K   T   D   R   E   K   Y   N   R   I   A
```

FIG. 1B

```
GCA CGG GAC CCT CCA GCA CAG TGT TCA GCA GGT CCT
 A   R   D   P   P   A   Q   C   S   A   G   P
GGG CCA AAT GAC AGT CCC TAT CAG GGT GGA GTA TTT
 G   P   N   D   S   P   Y   Q   G   G   V   F
CCA CCT AAG GTT GCA TTT ACA ACA AGA ATT TAT CAT
 P   P   K   V   A   F   T   T   R   I   Y   H
CTA CGA TCA CAG TGG TCT CCA GCA CTA ACT ATT TCA
 L   R   S   Q   W   S   P   A   L   T   I   S
AAT CCA GAT GAT CCT TTA GTG CCT GAG ATT GCT CGG
 N   P   D   D   P   L   V   P   E   I   A   R
CGG GAA TGG ACT CAG AAG TAT GCG ATG TAA      .
 R   E   W   T   Q   K   Y   A   M
```

FIG. 2A

```
1    ATG GCG GCC AGC AGG AGG CTG ATG AAG GAG CTT GAA GAA
     M   A   A   S   R   R   L   M   K   E   L   E   E

76   CAG GTT GAT GAA GCT AAT TTA TTG ACT TGG CAA GGG CTT
     Q   V   D   E   A   N   L   L   T   W   Q   G   L

151  TTC AGA ATC GAA ATC AAC TTT CCA GCA GAG TAC CCA TTC
     F   R   I   E   I   N   F   P   A   E   Y   P   F

226  CAC CCA AAC ATC GAC GAA AAG GGG CAG GTC TGT CTG CCA
     H   P   N   I   D   E   K   G   Q   V   C   L   P

301  ACC GAC CAA GTA ATC CAG TCC CTC ATA GCA CTG GTG AAT
     T   D   Q   V   I   Q   S   L   I   A   L   V   N

376  GCT GAA TAC TCT AAG GAC CGT AAA AAA TTC TGT AAG
     A   E   E   Y   S   K   D   R   K   K   F   C   K

451  CGA CCT GTG GAC TAA
     R   P   V   D   .
```

FIG. 2B

```
ATC CGC AAA TGT GGG ATG AAA AAC TTC CGT AAC ATC
 I   R   K   C   G   M   K   N   F   R   N   I
ATT GTT CCT GAC AAC CCT CCA TAT GAT AAG GGA GCC
 I   V   P   D   N   P   P   Y   D   K   G   A
AAA CCA CCG AAG ATC ACA TTT AAA ACA AAG ATC TAT
 K   P   P   K   I   T   F   K   T   K   I   Y
GTA ATT AGT GCC GAA AAC TGG AAG CCA GCA ACC AAA
 V   I   S   A   E   N   W   K   P   A   T   K
GAC CCC CAG CCT GAG CAC CCG CTT CGG GCT GAC CTA
 D   P   Q   P   E   H   P   L   R   A   D   L
AAT GCT GAA GAG TTT ACA AAG AAA TAT GGG GAA AAG
 N   A   E   E   F   T   K   K   Y   G   E   K
```

FIG. 3A

```
1    ATG ACA GTC CAA GCA CTA GGG CAC GAG AGT TCC
     M   T   V   Q   A   L   G   H   E   S   S

76   GAA CAA GTT CAG CCC AAG AAA AAG GAG GGA AAA
     E   Q   V   Q   P   K   K   K   E   G   K

151  AGA ATT CAG AAG GAA CTT GCA GAA ATC ACA TTG
     R   I   Q   K   E   L   A   E   I   T   L

226  ATT TAT GAA TGG AGG TCA ACT ATA TTG GGA CCC
     I   Y   E   W   R   S   T   I   L   G   P

301  ACC TTT TCA CCA GAC TAT CCG TTT AAA CCC CCT
     T   F   S   P   D   Y   P   F   K   P   P

376  AGC CAA GGT GTG ATC TGT CTG GAC ATC TTA AAG
     S   Q   G   V   I   C   L   D   I   L   K

451  TCC ATC TGC TCA CTT CTT ACA GAT TGC AAC CCT
     S   I   C   S   L   L   T   D   C   N   P

526  AAC AGA GGA GAG CAT GAC CGG ATG GAC AGA CAG
     N   R   G   E   H   D   R   M   D   R   Q
```

FIG. 3B

```
GAT GGA GAT CAA CGT GAA AGT GTT CAG CAA GAA CCA GAA AGA
 D   G   D   Q   R   E   S   V   Q   Q   E   P   E   R

ATA TCC AGC AAA ACC GCT GCT AAA TTG TCA ACT AGT GCT AAA
 I   S   S   K   T   A   A   K   L   S   T   S   A   K

GAC CCT CCT CCC AAC TGT AGT GCT GGA CCC AAA GGA GAC AAC
 D   P   P   P   N   C   S   A   G   P   K   G   D   N

CCA GGA TCT GTC TAT GAA GGA GGG GTG TTC TTT CTT GAC ATT
 P   G   S   V   Y   E   G   G   V   F   F   L   D   I

AAG GTT ACC TTC CGA ACA AGA TTT TTT CAC ATT TCT AAA ATT AAC
 K   V   T   F   R   T   R   F   F   H   I   S   K   I   N

GAC AAC TGG AGT CCG GCT TTA ACT ATT TCT AAA GTT CTC CTC
 D   N   W   S   P   A   L   T   I   S   K   V   L   L

GCT GAC CCT CTG GTG GGG AGC ATC GCC ACA CAG TAC ATG ACC
 A   D   P   L   V   G   S   I   A   T   Q   Y   M   T

TGG ACC AAG CGG TAC GCC ACA TAG .
 W   T   K   R   Y   A   T   .
```

FIG. 4

```
  1 MALKRIHKELNDLARDPPAQCSAGPVGDDMFHWQATIMGPNDSPYQGGVF    50
    ||||||:||:|||.|:.||.||||||||||||:|||||||.||||||||
  1 MALKRINKELQDLGRDPPAQCSAGPVGDDLFHWQATIMGPPDSPYQGGVF    50

51 FLTIHFPTDYLFKPPPKVAFTTRIYHPNINSNGSMCLDILRSQWSPALTIS  100
    |||||||||| ||||||||||||||||||||||||:|||||||||||||||
 51 FLTIHFPTDYPFKPPPKVAFTTRIYHPNINSNGSICLDILRSQWSPALTIS  100

101 KVLLSICSLXCDPNPDDPLVPEIARIYKTDREKYNRIAREWTQKYAM     147
    |||||||||| |||||||||||||||||||||||||:|||||||.||||
101 KVLLSICSLLCDPNPDDPLVPEIARIYKTDREKYNELAREWTRKYAM     147
```

FIG. 5

```
1   ..........MAASRRLMKELEEIRKCGMKNFRNIQVDEANLLTWQGLIVP  41
              ::|..:  ||...||:|.: |:::.|||.|.  .|:|
1   MMILLEVIPVPAEINISFELGDLKNCGVKAYENVECEETNLLKWTVLLIP   50

42  DNPPYDKGAFRIEINFPAEYPFKPPKITFKTKIYHPNIDEKGQVCLPVIS   91
    |..||.|||:::||||||.:|.||||:||.|.|.||||||.||.|.:|:
51  DKEPYNKGAFKVGITFPVDYPFKPPKVAFETKIYHPNVDEEGKFCLPIVT  100

92  AENWKPATKTDQVIQSLIALVNDPQPEHPLRADLAEEYSKDRKKFCKNAE  141
    |||||||||.:||.:|:|:|.|:|.|:.|||.||||..|:|.||||:
101 AENWKPATKTEQVMMALLSLINEPEPSHPIRADVAEEFQKDHKKFMKTAE  150

142 EFTKKYGEKRPVD  154
    |.|:||||||
151 EHTRKHAEKRPE.  162
```

FIG. 6

```
1   MTVQALGHESSDGDQRESVQQEPEREQVQPKKKEGKISSKTAAKLSTSAK  50
                                             .:.:
1   .................................................MSSSK   5

51  RIQKELAEITLDPPPNCSAGPKGDNIYEWRSTILGPPGSVYEGGVFFLDI  100
    || ||| || |||| ||||| :: || |||| ::|.|.:|||||.|||.|
6   RIAKELSDLERDPPTSCSAGPVGDDLYHWQASIMGPADSPYAGGVFFLSI  55

101 TFSPDYPFKPPPKVTFRTRFFHCNINSQVICLDDILKDNWSPALTISKVLL  150
    :.|||||||||| |:|:.||| |||:|||:|||||||||||||||:||||
56  HFPTDYPFKPPKISFTTKIYHPNINANGNICLDILKDQWSPALTLSKVLL  105

151 SICSLLTDCNPADPLVGSIATQYMTNRGEHDRMDRQWTKRYAT  193
    |||||||| ||| |||| .|.:|     |.|:...: .:|||||.
106 SICSLLTDANPDDPLVPEIAHIYKTDRPKYEATAREWTKKYAV  148
```

UBIQUITIN CONJUGATING ENZYMES 8 AND 9

This application is a Division of application Ser. No. 08/464,342 filed Jun. 5, 1995, now U.S. Pat. No. 5,650,313, which is a continuation-in-part of International Application PCT/US95/01250, filed Jan. 31, 1995, under 35 U.S.C. §120, now abandoned.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are Ubiquitin Conjugating Enzymes 7, 8 and 9, sometimes hereinafter referred to as "UCE 7, 8 and 9." The invention also relates to modulating the action of such polypeptides.

Mammalian cells contain two distinct proteolytic pathways that are involved in different aspects of protein breakdown. One of these is ubiquitin-dependent, it is a major pathway in eukaryotes involved in the selective degradation of abnormal and short-lived proteins. Ubiquitin is a highly conserved 76 amino acid residue protein present in eukaryotic cells either free or covalently attached to a great variety of proteins. The post-translational attachment of ubiquitin to other proteins is catalyzed by ubiquitin conjugating enzymes and involves the formation of an isopeptide bond between the C-terminal glycine residue of ubiquitin and the epsilon-amino group of a lysine-residue in an acceptor protein.

Ubiquitin-protein conjugation is highly selective and is required for a surprising variety of cellular functions. Genetic studies in yeast showed that ubiquitin conjugating enzymes are required for DNA repair, induced mutagenesis, sporulation, repression of retrotransposition, cell cycle progression, cell viability, heat shock resistance, cadmium tolerance, and peroxisome biogenesis. Several in vivo substrates have been identified, including histones, actin, cell surface receptors, the MATα2 transcriptional repressor, the tumor suppressor protein p53, the Mos kinase and cyclins. UCE 7, 8 and 9 may play a major role in selective protein degradation in human cells.

The ubiquitin gene is one of the genes known to be stimulated during the apoptotic death program and ubiquitin of nuclear proteins might be involved in chromatin disorganization and oligonucleosomal fragmentation, which are among the key events occurring in apoptosis. Apoptosis, the classical type of programmed cell death, can be triggered in many cell types by widely diverse stimuli, for example, gamma rays at low doses can induce apoptosis in vitro in interphase human lymphocytes. In this type of apoptosis induction, activated gene expression is necessary for the fulfillment of the death program. It has been reported (Delic, J., et al., Mol. Cell Biol., 13:4875, 83 (1993)) that there is a relationship between ubiquitin gene expression or ubiquitination and gamma-irradiation-mediated apoptosis in normal circulating human lymphocytes. In this report it has been demonstrated that the ubiquitin mRNA level is increased as a consequence of the activation of ubiquitin gene transcription 15 to 90 minutes after initiation of apoptosis; specifically, in apoptotic cells, and not in all irradiated cells, nuclear proteins are highly ubiquitinated; and ubiquitin sequence-specific antisense oligonucleotide inhibition results in a decreased level of ubiquitinated nuclear proteins and considerably diminishes the proportion of cells exhibiting the apoptotic death pattern.

Perturbations of ubiquitin system can also induce a programmed necrotic response in plants such as leaf curling, vascular tissue alterations and necrotic lesions.

Ubiquitin can inhibit the cytotoxic properties of platelets and the production of oxygen metabolites by these cells. Moreover, this molecule is able to act as a proaggregating factor and seems of a great interest in pathologies involving defects in platelet aggregation. Ubiquitin also plays a role in the regulation of immunological disorders in which platelets seem to be implicated such as hymenoptera venom hypersensitivity and aspirin-sensitive asthma, since in both situations, ubiquitin is able to inhibit the cytotoxic function of platelets.

Ubiquitin has also been shown to be increased in patients with Alzheimer's disease (Taddei, N., et al., Neurosci. Lett., 151:158–61 (1993)). This study concerned the amount of soluble ubiquitin in different cortical and subcortical regions of brains from patients with Alzheimer's disease compared to the amount in a normal brain. The soluble ubiquitin content was significantly higher in pathological tissue than in normal tissue. The primary structure of ubiquitin isolated from brain tissue affected by Alzheimer's degenerative processes was determined and resulted to be identical to normal human ubiquitin. This report suggests that an impairment of the process of intracellular, ubiquitin-dependent proteolysis might play an important role in the pathogenesis of this neurodegenerative disease.

Ubiquitin-proteasome system also plays a major role in specific processing and subsequent presentation of MHC class I-restricted antigens.

Maturation of the p105 NF-KB precursor into the active p50 subunit of the transcriptional activator also proceeds in a ubiquitin and proteasome-dependent manner. Furthermore, inhibitors to the proteasome block degradation of IkBa and thus prevent tumor necrosis factor alpha induced activation of NF-KB and its entry into the nucleus.

The unstable c-Jun, but not the stable v-Jun, is multi-ubiquitinated and degraded. The escape of the oncogenic v-Jun from ubiquitin-dependent degradation suggests a route to the malignant transformation. Another proto-oncoprotein, c-Mos, is also degraded by the ubiquitin system.

The human papilloma virus (HPV) derived E6 proteins stimulate ATP and ubiquitin dependent conjugation and degradation of p53, such a mechanism could explain the extremely low levels of p53 observed in HPV-transformed cervical carcinoma lines and propose a mechanism for the tumorigenicity of these onco-proteins.

Several cell surface receptors, including the lymphocyte homing receptor, growth hormone receptor, and growth factor receptor (PDGF, steel factor) were also found to be modified by ubiquitin.

The polypeptides of the present invention have been putatively identified as UCE 7, 8 and 9. This identification has been made as a result of amino acid sequence homology.

In accordance with one aspect of the present invention, there are provided novel mature polypeptides which are UCE 7, 8 and 9, as well as biologically active and diagnostically or therapeutically useful fragments, analogs and derivatives thereof. The polypeptides of the present invention are of human origin.

In accordance with another aspect of the present invention, there are provided isolated nucleic acid molecules encoding UCE 7, 8 and 9, including mRNAs, DNA's, cDNA's, genomic DNA, as well as biologically active and diagnostically or therapeutically useful fragments, analogs and derivatives thereof.

In accordance with yet a further aspect of the present invention, there is provided a process for producing such polypeptides by recombinant techniques comprising culturing recombinant prokaryotic and/or eukaryotic host cells, containing a human UCE 7, 8 or 9 nucleic acid sequence, under conditions promoting expression of said proteins and subsequent recovery of said proteins.

In accordance with yet a further aspect of the present invention, there is provided a process for utilizing such polypeptides, or polynucleotides encoding such polypeptides for therapeutic purposes, for example, to treat malignant transformations, immunological disorders, to mark unwanted cells for cell death, and to screen for agonists and antagonists which interact with the polypeptides.

In accordance with yet a further aspect of the present invention, there are provided antibodies against such polypeptides.

In accordance with yet another aspect of the present invention, there are provided antagonists to such polypeptides, which may be employed to inhibit the action of such polypeptides, for example, in the treatment of atrophying skeletal muscle, cervical carcinoma and certain tumors, Alzheimer's disease, endemic pemphigus foliaceus and African swine fever.

In accordance with another aspect of the present invention, there are provided nucleic acid probes comprising nucleic acid molecules of sufficient length to specifically hybridize to UCE 7, 8 and 9 sequences.

In accordance with another aspect of the present invention, there is provided a process for utilizing such polypeptides, or polynucleotides encoding such polypeptides, for in vitro purposes related to scientific research, synthesis of DNA and manufacture of DNA vectors.

In accordance with yet another aspect of the present invention, there are provided diagnostic assays for detecting diseases or susceptibility to diseases related to mutations in UCE 7, 8 or 9 nucleic acid sequences or over-expression of the polypeptides encoded by such sequences.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A and 1B, collectively illustrates the CDNA sequence and the corresponding deduced amino acid sequence of UCE 7 polypeptide. The standard one-letter abbreviations for amino acids is used. Sequencing was performed using a 373 Automated DNA sequencer (Applied Biosystems, Inc.). Sequencing accuracy is predicted to be greater than 97% accurate.

FIGS. 2A and 2B, collectively, illustrate the cDNA sequence and the corresponding deduced amino acid sequence of UCE 8 polypeptide.

FIGS. 3A and 3B, collectively, illustrates the cDNA sequence and the corresponding deduced amino acid sequence of UCE 9 polypeptide.

FIG. 4 illustrates the amino acid sequence homology between UCE 7 and UCE from *Drosophila melanogaster.*

FIG. 5 illustrates the amino acid sequence homology between UCE 8 and the Caenorhabditis elegans UCE gene product.

FIG. 6 illustrates the amino acid sequence homology between UCE 9 and UCE from *Saccharomyces cerevisiae.*

In accordance with an aspect of the present invention, there is provided an isolated nucleic acid (polynucleotide) which encodes for the mature polypeptides having the deduced amino acid sequence of FIGS. 1A–1B, 2A–2B and 3A–3B (SEQ ID No. 2, 4 and 6), or for the mature polypeptides encoded by the cDNAs of the clone deposited as ATCC Deposit No. 75877, 75876 and 75878 on Aug. 29, 1994 encoding UCE 7, 8 and 9, respectively.

The ATCC numbers referred to above are directed to biological deposits with the ATCC, 10801 University Blvd. Manassas, Va. 20110. Since the strains referred to are beng maintained under the terms of the Budapest Treaty, each of them will be made available to a patent office signatory to the Budapes Treaty.

A polynucleotide encoding a UCE 7 polypeptide of the present invention may be obtained from tumor testis, activated T-cells and chondrosarcoma. The polynucleotide of this invention was discovered in a CDNA library derived from Raji cells (cycloheximide treated). It is structurally related to the human ubiquitin conjugating enzyme family. It contains an open reading frame encoding a protein of 147 amino acid residues. The protein exhibits the highest degree of homology to UCE from Drosophila melanogastor with 93% identity and 96% similarity over a 147 amino acid stretch.

A polynucleotide encoding a UCE 8 polypeptide of the present invention may be obtained from osteoclastoma, tumor testis and activated T-cells. The polynucleotide of this invention was discovered in a cDNA library derived from human fetal brain. It is structurally related to the human ubiquitin conjugating enzyme family. It contains an open reading frame encoding a protein of 154 amino acid residues. The protein exhibits the highest degree of homology to UCE from Caenorhabditis elegans with 55% identity and 78% similarity over a 154 amino acid stretch.

A polynucleotide encoding a UCE 9 polypeptide of the present invention may be obtained from embryo, smooth muscle and greater omentum. The polynucleotide of this invention was discovered in a cDNA library derived from human greater omentum. It is structurally related to the human ubiquitin conjugating enzyme family. It contains an open reading frame encoding a protein of 193 amino acid residues. The protein exhibits the highest degree of homology to UCE from *S. cerevisiae* with 61% identity and 72% similarity over a 193 amino acid stretch.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1B, 2A–2B and 3A–3B (SEQ ID No. 1, 3 and 5) or that of the deposited clone or may be a different coding sequence which coding sequence, as a result of the redundancy or degeneracy of the genetic code, encodes the same mature polypeptides as the DNA of FIGS. 1A–1B, 2A–2B and 3A–3B (SEQ ID No. 1, 3 and 5) or the deposited CDNA.

The polynucleotide which encodes for the mature polypeptides of FIGS. 1A–1B, 2A–2B and 3A–3B (SEQ ID No. 2, 4 and 6) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptides as well as a polynucleotide which includes additional coding and/or non-coding sequence.

The present invention further relates to variants of the hereinabove described polynucleotides which encode for fragments, analogs and derivatives of the polypeptide having the deduced amino acid sequences of FIGS. 1A–1B, 2A–2B and 3A–3B (SEQ ID No. 2, 4 and 6) or the polypeptides encoded by the cDNA(s) of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptides as shown in FIGS. 1A–1B, 2A–2B and 3A–3B (SEQ ID No. 2, 4 and 6) or the same mature polypeptide encoded by the cDNA(s) of the deposited clone as well as variants of such polynucleotides which variants encode for a fragment, derivative or analog of the polypeptides of FIGS. 1A–1B, 2A–2B and 3A–3B (SEQ ID No. 2, 4 and 6) or the polypeptides encoded by the cDNA(s) of the deposited clone(s). Such nucleotide variants include deletion variants, substitution variants and addition or insertion variants.

As hereinabove indicated, the polynucleotide may have a coding sequence which is a naturally occurring allelic variant of the coding sequences shown in FIGS. 1A–1B, 2A–2B and 3A–3B (SEQ ID No. 1, 3 and 5) or of the coding sequence of the deposited clones. As known in the art, an allelic variant is an alternate form of a polynucleotide sequence which may have a substitution, deletion or addition of one or more nucleotides, which does not substantially alter the function of the encoded polypeptides.

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length CDNA and to isolate other cDNAs which have a high sequence similarity to the gene or similar biological activity. Probes of this type preferably have at least 30 bases and may contain, for example, 50 or more bases. The probe may also be used to identify a CDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1A and 1B, collectively, (SEQ ID NO:1) or the deposited cDNKA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to UCE 7, 8 and 9 polypeptides which have the deduced amino acid sequence of FIGS. 1A–1B, 2A–2B and 3A–3B (SEQ ID No. 2, 4 and 6) or which has the amino acid sequence encoded by the deposited cDNAs, as well as fragments, analogs and derivatives of such polypeptide.

The terms "fragment" "derivative" and "analog" when referring to the polypeptides of FIGS. 1A–1B, 2A–2B and 3A–3B (SEQ ID No. 2, 4 and 6) or that encoded by the deposited cDNA(s), means polypeptides which retain essentially the same biological function or activity as such polypeptides. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragment, derivative or analog of the polypeptides of FIGS. 1A–1B, 2A–2B and 3A–3B (SEQ ID No. 2, 4 and 6) or that encoded by the deposited cDNA(s) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particulars the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the UCE 7, 8 and 9 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotides may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct MRNA synthesis. As representative examples of such promoters, there may be mentioned: LTR or SV40 promoter, the $E.$ $coli.$ lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the polypeptide.

As representative examples of appropriate hosts, there may be mentioned: bacterial cells, such as $E.$ $coli,$ Streptomyces, $Salmonella$ $typhimurium;$ fungal cells, such as yeast; insect cells such as Drosophila S2 and Spodoptera Sf 9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, PSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation, initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The UCE 7, 8 and 9 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The UCE 7, 8 and 9 polypeptides and agonists and antagonists which are polypeptides, described below, may also be employed in accordance with the present invention by expression of such polypeptides in vivo, which is often referred to as "gene therapy".

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques, Vol.* 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PES01, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the UCE 7, 8 and 9 polypeptides are being expressed intra-cellularly via gene therapy, they may be employed to provide a signal for the lymphocyte homing receptor thereby regulating lymphocyte trafficking. The growth hormone receptor also utilizes ubiquitin to signal ligands, and, therefore, the UCE 7, 8 and 9 polypeptides may be employed to regulate activation of the growth receptor.

UCE 7, 8 and 9 polypeptides may be employed to overcome many viral infections by overcoming the suppressed programmed cell death induced by these viruses, since programmed cell death may be one of the primary antiviral defense mechanisms of cells.

UCE 7, 8 and 9 polypeptides may also be employed to treat immuno-suppression related disorders, such as AIDS, by targeting virus infected cells for cell death.

UCE 7, 8 and 9 may also be employed to inhibit the cytotoxic properties of platelets and the production of oxygen metabolites by platelets. These polypeptides may also be employed to regulate immunological disorders in which platelets seem to be involved, for example, hymenoptera venom hypersensitivity and aspirin-sensitive asthma.

UCE 7, 8 and 9 may also be employed to treat malignant transformation because proto-oncoproteins c-Mos and v-Jun are degraded in a ubiquitin-dependent manner.

In accordance with yet a further aspect of the present invention, there is provided a process for utilizing such polypeptides, or polynucleotides encoding such polypeptides, for in vitro purposes related to scientific research, synthesis of DNA, manufacture of DNA vectors and for the purpose of providing diagnostics and therapeutics for the treatment of human disease.

The present invention further provides a method of screening compounds to identify those which enhance (agonists) or block (antagonists) the activity of the UCE 7, 8 and 9 enzymes. An example of such a method comprises combining reactants in the presence of UCE 7, 8 or 9 and a compound to be screened under conditions where ubiquitin is normally transferred to a protein substrate. The reactants comprise [$I^{125}$]ubiquitin, ATP, and a protein substrate, for example, histones. Under normal conditions, ubiquitin would be transferred to the protein substrate and this transfer is catalyzed by the UCE 7, 8 or 9 enzymes. The amount of labeled substrate, i.e., substrate with labeled ubiquitin attached thereto, could then be measured to determine if the compound to be screened enhanced or blocked the catalysis of this reaction by UCE 7, 8 or 9.

Human UCE 7, 8 and 9 are produced and function intra-cellulary, therefore, any antagonists must be intracellular. Examples of potential UCE 7, 8 or 9 antagonists include antibodies which are produced intra-cellularly. For example, an antibody identified as antagonizing UCE 7, 8 and 9 may be produced intra-cellularly as a single chain antibody by procedures known in the art, such as transforming the appropriate cells with DNA encoding the single chain antibody to prevent the function of UCE 7, 8 or 9.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of UCE 7, 8 and 9. The antisense RNA oligonucleotide hybridizes to the mRNA in vivo and blocks translation of the mRNA molecule into the UCE 7, 8 and 9 polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of UCE 7, 8 and 9.

Yet another potential antagonist includes a mutated form, or mutein, of UCE 7, 8 or 9 which recognizes substrate but does not catalyze ubiquitination and, therefore, acts to prevent UCE 7, 8 or 9 from functioning.

Potential antagonists also include small molecules which are able to pass through cell membranes and bind to the catalytic site of the polypeptide thereby making the catalytic site inaccessible to substrate such that normal biological activity is prevented.

The antagonists may be employed to treat a host of diseases in which UCE 7, 8 and 9 catalyze the transfer of ubiquitin to a substrate and marks that substrate for cell death. An example is Alzheimer's disease, wherein the ubiquitin content is found to be significantly higher in tissue derived from patients with Alzheimer's disease than in normal tissue.

The antagonists may also be employed to treat atrophying skeletal muscle, since the atrophying of this muscle occurs due to these cells being marked for cell death with ubiquitin.

The antagonists may also be employed to treat a patient infected with the African swine fever virus which proliferates in the host and produces a conjugating enzyme to kill cells in a attempt to overtake the host's regulatory mechanisms. Accordingly, inhibiting UCE 7, 8 and 9 prevents the proliferation of the African swine fever virus.

The antagonists may also be employed to treat a blistering skin disease called endemic pemphigus foliaceus (EPF) which is also a type of autoimmune disorder, which is thought to degrade skin through the use of a ubiquitin conjugating enzyme.

The antagonists may also be employed to treat certain malignant transformations, for example, Human papilloma virus (HPV) transformed cervical carcinoma which stimulates the ubiquitin-dependent degradation of p53, a tumor suppressor protein. Further, epidermal tumors in mice have been found to over-express ubiquitin genes.

The small molecule agonists and antagonists may be employed in combination with a suitable pharmaceutical carrier. Such compositions comprise a therapeutically effective amount of the agonists or antagonists and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

This invention is also related to the use of the UCE genes as a diagnostic. Detection of a mutated form of UCE 7, 8 or 9 will allow a diagnosis of a disease or a susceptibility to a disease which results from underexpression of these genes, for example, tumors and immune disorders.

Individuals carrying mutations in the human UCE 7, 8 or 9 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding UCE 7, 8 or 9 can be used to identify and analyze mutations. For example, deletions and insertions can be detected by a change in size of the amplified product in comparison to the normal genotype. Point mutations can be identified by hybridizing amplified DNA to radiolabeled UCE 7, 8 or 9 RNA or alternatively, radiolabeled UCE 7, 8 or 9 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of UCE 7, 8 or 9 protein in various tissues since an over-expression of the proteins compared to normal control tissue samples can detect the presence of tumors. Assays used to detect levels of UCE 7, 8 or 9 protein in a sample derived from a host are well-known to those of skill in the art and include radioimmunoassays, competitive-binding assays, Western Blot analysis and preferably an ELISA assay. An Elisa assay initially comprises preparing an antibody specific to the UCE 7, 8 or 9 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any UCE 7, 8 or 9 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to UCE 7, 8 or 9 protein. Unattached reporter antibody is then washed out. Peroxidase substrates are then added to the dish and the amount of color developed in a given time period is a measurement of the amount of protein present in a given volume of patient sample when compared against a standard curve.

A competition assay may be employed wherein antibodies specific to UCE 7, 8 or 9 protein are attached to a solid support and labeled UCE 7, 8 or 9 and a sample derived from the host are passed over the solid support and the amount of label detected attached to the solid support can be correlated to a quantity in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment, as described in Sambrook et al., Molecular Cloning: A laboratory Manual, Second Edition, Cold Spring Harbor, N.Y. (1989).

Size separation of the cleaved fragments is performed using 8 percent polyacrylamide gel described by Goeddel, D. et al., Nucleic Acids Res., 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of UCE 7

The DNA sequence encoding UCE 7, ATCC #75877, was initially amplified using PCR oligonucleotide primers corresponding to the 5' sequences of the processed UCE 7 protein and the vector sequences 3' to the UCE 7 gene. Additional nucleotides corresponding to UCE 7 were added to the 5' and 3' end sequences respectively. The forward oligonucleotide primer has the sequence 5' CCCGGATCCGCTTCGAAGAGAATCCACAAG 3' (SEQ ID No. 7) contains a Bam HI restriction enzyme site followed by 21 nucleotides of UCE 7 coding sequence starting from the presumed terminal amino acid of the processed protein codon. The reverse primer 5' GCGCAAGCTTTTACATCGCATACTTCTGAGTCC 3' (SEQ ID No. 8) contains a Hind III site, a stop codon plus 20 nucleotides of UCE 7. The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/O), a ribosome binding site (RBS), a 6-His tag and single restriction enzyme sites. pQE-9 was then digested with Bam H1 and Hind III. The amplified sequences were ligated into pQE-9 and were inserted in frame with the sequence encoding for the histidine tag and the RBS. The ligation mixture was then used to transform E. coli strain ml5/pREP4 (Qiagen) by the procedure described in Sambrook, J. et al., Molecular Cloning: A Laboratory Manual, Cold Spring Laboratory Press, (1989). M15/pREP4 contains multiple copies of the plasmid pREP4, which expresses the laci repressor and also confers kanamycin resistance (Kan'). Transformants are identified by their ability to grow on LB plates and ampicillin/kanamycin resistant colonies were selected. Plasmid DNA was isolated and confirmed by restriction analysis.

Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized UCE 7 was purified from this solution by chromatography on a Nickel-Chelate column under conditions that allow for tight binding by proteins containing the 6-His tag (Hochuli, E. et al., J. Chromatography 411:177–184 (1984)). UCE 7 was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Bacterial Expression and Purification of UCE 8

The DNA sequence encoding UCE 8, ATCC #75876, was initially amplified using PCR oligonucleotide primers corresponding to the 5' sequences of the processed UCE 8 protein and the vector sequences 3' to the UCE 8 gene. Additional nucleotides corresponding to UCE 8 were added to the 5' and 3' end sequences, respectively. The forward oligonucleotide primer has the sequence 5' CCCGGATC-CGCGGCCAGCAGGAGGCTGATG 3' (SEQ ID No. 9) contains a Bam HI restriction enzyme site followed by 21 nucleotides of UCE 8 coding sequence starting from the presumed terminal amino acid of the processed protein codon. The reverse primer 5' GCGCAAGCTTTTAGTCCA-CAGGTCG 3' (SEQ ID No. 10) contains a Hind III site, a stop codon plus 15 nucleotides of UCE 8 coding sequence. The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/O), a ribosome binding site (RBS), a 6-His tag and single restriction enzyme sites. pQE-9 was then digested with Bam H1 and Hind III. The amplified sequences were ligated into pQE-9 and were inserted in frame with the sequence encoding for the histidine tag and the RBS. The ligation mixture was then used to transform *E. coli* strain m15/pREP4 (Qiagen) by the procedure described in Sambrook, J. et al., Molecular Cloning: A Laboratory Manual, Cold Spring Laboratory Press, (1989). M15/pREP4 contains multiple copies of the plasmid pREP4, which expresses the laci repressor and also confers kanamycin resistance (Kan'). Transformants are identified by their ability to grow on LB plates and ampicillin/kanamycin resistant colonies were selected. Plasmid DNA was isolated and confirmed by restriction analysis.

Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized UCE 8 was purified from this solution by chromatography on a Nickel-Chelate column under conditions that allow for tight binding by proteins containing the 6-His tag (Hochuli, E. et al., J. Chromatography 411:177–184 (1984)). UCE 8 was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 3

Bacterial Expression and Purification of UCE 9

The DNA sequence encoding UCE 9, ATCC #75878, is initially amplified using PCR oligonucleotide primers corresponding to the 5' sequences of the processed UCE 9 protein and the vector sequences 3' to the UCE 9 gene. Additional nucleotides corresponding to UCE 9 are added to the 5' and 3' end sequences respectively. The forward oligonucleotide primer has the sequence 5' GCGCGGATC-CACAGTCCAAGCACTAGGGC 3' (SEQ ID No. 11) contains a Bam HI restriction enzyme site followed by 19 nucleotides of UCE 9 coding sequence starting from the presumed terminal amino acid of the processed protein codon. The reverse primer 5' GCGCAAGCTTCTATGTG-GCGTACCGCTTGG 3' (SEQ ID No. 12) contains complementary sequences to a Hind III site and is followed by 20 nucleotides of UCE 9 including the translational stop codon. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (AMp'), a bacterial origin of replication (ori), an IPTG-regulatable promoter operator (P/O), a ribosome binding site (RBS), a 6-His tag and restriction enzyme sites. pQE-9 is then digested with Bam H1 and Hind III. The amplified sequences are ligated into pQE-9 and are inserted in frame with the sequence encoding for the histidine tag and the RBS. The ligation mixture is then used to transform *E. coli* strain m15/pREP4 (Qiagen) by the procedure described in Sambrook, J. et al., Molecular Cloning: A Laboratory Manual, Cold Spring Laboratory Press, (1989). M15/pREP4 contains multiple copies of the plasmid pREP4, which expresses the laci repressor and also confers kanamycin resistance (Kan'). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized UCE 9 is purified from this solution by chromatography on a Nickel-Chelate column under conditions that allow for tight binding by proteins containing the 6-His tag (Hochuli, E. et al., J. Chromatography 411:177–184 (1984)). UCE 9 is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 4

Cloning and Expression of UCE 7 Using the Baculovirus Expression System

The DNA sequence encoding the full length UCE 7 protein, ATCC #75877, is amplified using PCR oligonucleotide primers corresponding to the 5' and 3' sequences of the gene:

The forward primer has the sequence 5' GCGCGGATC-CACCAT GGCTCTGAAGAGAATCC 3' (SEQ ID No. 13) and contains a Bam HI restriction enzyme site (in bold) followed by 3 nucleotides resembling an efficient signal for the initiation of translation in eukaryotic cells (Kozak, M., J. Mol. Biol., 196:947–950 (1987) which is just behind the first 15 nucleotides of the UCE 7 gene (the initiation codon for translation "ATG" is underlined).

The reverse primer has the sequence 5' GCGCTCTAGAT-TACA TCGCATACTTCTGAGRCC 3' (SEQ ID No. 14)

and contains the cleavage site for the restriction endonuclease XbaI and 23 nucleotides complementary to the 3' translated sequence of the UCE 7 gene. The amplified sequences are isolated from a 1% agarose gel using a commercially available kit ("Geneclean," BIO 101 Inc., La Jolla, Calif.). The fragment is then digested with the endonucleases Bam HI and XbaI and then purified again on a 1% agarose gel. This fragment is designated F2.

The vector pRG1 (modification of pVL941 vector, discussed below) is used for the expression of the UCE 7 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Bam HI and XbaI. The polyadenylation site of the simian virus (SV)40 is used for efficient polyadenylation. For an easy selection of recombinant viruses the beta-galactosidase gene from $E.\ coli$ is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes Bam HI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. $E.\ coli$ DH5α cells are then transformed and bacteria identified that contained the plasmid (pBac UCE7) with the UCE 7 gene using the enzymes Bam HI and XbaI. The sequence of the cloned fragment is confirmed by DNA sequencing.

5 $\mu$g of the plasmid pBac UCE 7 is cotransfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 $\mu$g of BaculoGold™ virus DNA and 5 $\mu$g of the plasmid pBac UCE7 are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-UCE-7 at a multiplicity of infection (MOI) of 2. Six hours later the medium is removed and replaced with SF900 II medium minus methionine and cysteine (Life Technologies Inc., Gaithersburg). 42 hours later 5 $\mu$Ci of $^{35}$S-methionine and 5 $\mu$Ci $^{35}$S cysteine (Amersham) are added. The cells are further incubated for 16 hours before they are harvested by centrifugation and the labelled proteins visualized by SDS-PAGE and autoradiography.

EXAMPLE 5

Cloning and Expression of UCE 8 Using the Baculovirus Expression System

The DNA sequence encoding the full length UCE 8 protein, ATCC #75876, is amplified using PCR oligonucleotide primers corresponding to the 5' and 3' sequences of the gene:

The forward primer has the sequence 5' GCGCGGATC-CACCAT GGCGGCCAGCAGGAGGCT 3' (SEQ ID No. 15) and contains a Bam HI restriction enzyme site (in bold) followed by 3 nucleotides resembling an efficient signal for the initiation of translation in eukaryotic cells (Kozak, M., J. Mol. Biol., 196:947–950 (1987) and which is just behind the first 17 nucleotides of the UCE 8 gene (the initiation codon for translation "ATG" is underlined).

The reverse primer has the sequence 5' GCGCTCTA-GATTAGT CCACAGGTCG 3' (SEQ ID No. 16) and contains the cleavage site for the restriction endonuclease XbaI and 15 nucleotides complementary to the 3' translated sequence of the UCE 8 gene. The amplified sequences are isolated from a 1% agarose gel using a commercially available kit ("Geneclean," BIO 101 Inc., La Jolla, Calif.). The fragment is then digested with the endonucleases Bam HI and XbaI and then purified again on a 1% agarose gel. This fragment is designated F2.

The vector pRG1 (modification of pVL941 vector, discussed below) is used for the expression of the UCE 8 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Bam HI, SmaI, XbaI, BglII and Asp718. The polyadenylation site of the simian virus (SV)40 is used for efficient polyadenylation. For an easy selection of recombinant viruses the beta-galactosidase gene from $E.\ coli$ is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of PRG1 such as pAc373, pVL941 and pAcIM1 (Luckow, V. A. and Summers, M. D., Virology, 170:31–39).

The plasmid is digested with the restriction enzymes Bam HI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E. coli HB101 cells are then transformed and bacteria identified that contained the plasmid (pbac UCE 8) with the UCE 8 gene using the enzymes Bam HI and XbaI. The sequence of the cloned fragment is confirmed by DNA sequencing.

5 µg of the plasmid pBac UCE 8 is cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBac UCE 8 are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-UCE 8 at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labelled proteins visualized by SDS-PAGE and autoradiography.

EXAMPLE 6

Cloning and Expression of UCE 9 Using the Baculovirus Expression System

The DNA sequence encoding the full length UCE 9 protein, ATCC #75878, is amplified using PCR oligonucleotide primers corresponding to the 5' and 3' sequences of the gene:

The forward primer has the sequence 5' GATCGGATC-CACCAT GACAGTCCAAGCACTAG 3' (SEQ ID No. 17) and contains a Bam HI restriction enzyme site (in bold) followed by 3 nucleotides resembling an efficient signal for the initiation of translation in eukaryotic cells (Kozak, M., J. Mol. Biol., 196:947–950 (1987) and just behind the first 15 nucleotides of the UCE 9 gene (the initiation codon for translation "ATG" is underlined).

The reverse primer has the sequence 5' GCGCTCTA-GACTATG TGGCGTACCGCTTGG 3' (SEQ ID No. 18) and contains the cleavage site for the restriction endonuclease XbaI and 20 nucleotides complementary to the 3' translated sequence of the UCE 9 gene. The amplified sequences are isolated from a 1% agarose gel using a commercially available kit ("Geneclean," BIO 101 Inc., La Jolla, Calif.). The fragment is then digested with the endonucleases Bam HI and XbaI and then purified again on a 1% agarose gel. This fragment is designated F2.

The vector pRG1 (modification of pVL941 vector, discussed below) is used for the expression of the UCE 9 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Bam HI and XbaI. The polyadenylation site of the simian virus (SV)40 is used for efficient polyadenylation. For an easy selection of recombinant viruses the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes Bam HI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E. coli DH5α cells are then transformed and bacteria identified that contained the plasmid (pBac UCE9 ) with the UCE 9 gene using the enzymes Bam HI and XbaI. The sequence of the cloned fragment is confirmed by DNA sequencing.

5 µg of the plasmid pBac UCE 9 is cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBac UCE 9 are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Fppendorf pipette. The agar containing the recombinant viruses is then resuspended in an Eppendorf tube containing 200 μl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-UCE 9 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 7

Expression of Recombinant UCE 7 in COS Cells

The expression of plasmid, UCE 7 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire UCE 7 gene and an HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding UCE 7, ATCC #75877, is constructed by PCR using two primers: the 5' primer 5' GCGCGGATCCACCATGGCTCTGAAGAGAATCC 3' (SEQ ID No. 19) has a Bam HI site followed by 15 nucleotides of UCE 7 coding sequence starting from the initiation codon. The reverse primer 5' GCGCTCTAGAT-CAAGCGTAGTCTGGGACGTCGTATGGG-TACATCGCATACTTCTGAG3' (SEQ ID No. 20) contains complementary sequences to an XbaI site, translation stop codon, HA tag and the last 17 nucleotides of the UCE 7 coding sequence (not including the stop codon). Therefore, the PCR product contains a Bam HI site, UCE 7 coding sequence followed by HA tag fused in frame, a translation termination stop codon next to the HA tag, and an XbaI site. The PCR amplified DNA fragment and the vector, pcDNAI/Amp, are digested with Bam HI and XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant UCE 7, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the UCE 7-HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 8

Expression of Recombinant UCE 8 in COS Cells

The expression of plasmid, UCE 8-HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entir UCE 8 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding UCE 8, ATCC #75876, is constructed by PCR using two primers: the 5' primer 5' GCGCGGATCCACCATGGCGGCCAGCAGGAGGC 3' (SEQ ID No. 21) and contains a Bam HI site followed by 3 nucleotides resembling a Kozak sequence plus 19 nucleotides of UCE 8 coding sequence starting from the initiation codon; the 3' sequence 5' GCGCTCTAGATCAAGCG TAGTCTGGGACGTCGTATGGG'AGTCCACAGGTCG 3' (SEQ ID No. 22) contains complementary sequences to an XbaI site, translation stop codon, HA tag and the last 12 nucleotides of the UCE 8 coding sequence (not including the stop codon). Therefore, the PCR product contains a Bam HI site, UCE-8 coding sequence followed by HA tag fused in frame, a translation termination stop codon next to the HA tag, and an XbaI site. The PCR amplified DNKA fragment and the vector, pcDNAI/Amp, are digested with Bam HI and XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNKA is isolated from transformants and examined by restriction analysis for the presence of the correct fragment. For expression of the recombinant UCE-8, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the UCE 8-HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1t NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 9

Expression of Recombinant UCE 9 in COS Cells

The expression of plasmid, pUCE 9-HA is derived from a vector pcDNAI/Amp (Invitrogen) containing: 1) SV40 origin of replication, 2) ampicillin resistance gene, 3) E. coli replication origin, 4) CV promoter followed by a polylinker region, a SV40 intron and polyadenylation site. A DNA fragment encoding the entire UCE 9 protein and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding UCE 9, ATCC #75878, is constructed by PCR using two primers: the 5' primer 5' GATCGGATCCACCATGACAGTCCAAGCACTAG 3' (SEQ ID No. 23) contains a Bam HI site followed by 3 nucleotides resembling a Kozak sequence plus 19 nucleotides of UCE 9 coding sequence starting from the initiation codon; the 3' sequence 5' GCGCTCTAGATCAAGCG-TAGTCTGGGACGTCGTATGGGTATGTG-GCGTACCGCTTGG3' (SEQ ID No. 24) contains complementary sequences to an XbaI site, translation stop codon, HA tag and the last 17 nucleotides of the UCE 9 coding sequence (not including the stop codon). Therefore, the PCR product contains a Bam HI site, UCE 9 coding sequence followed by HA tag fused in frame, a translation termination stop codon next to the HA tag, and an XbaI site. The PCR amplified DNA fragment and the vector, pcDNAI/Amp, are digested with Bam HI and XbaI restriction enzyme and ligated. The ligation mixture is transformed into E. coli strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant UCE 9, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the UCE 9-HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 10

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer $further includes a HindIII site. Equal quantities of the Moloney murine sarcoma virus linear backbone and the amplified $EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising a member selected from the group consisting of:
   (a) a polypeptide as set forth as amino acids 1 to 154 of SEQ ID NO:4;
   (b) a polypeptide as set forth as amino acids 2 to 154 of SEQ ID NO-4;
   (c) a polypeptide encoded by the human cDNA in ATCC Deposit No: 75876;
   (d) a polypeptide encoded by the human cDNA in ATCC Deposit No. 75876, except the N-terminal methionine;
   (e) a mature polypeptide encoded by the human cDNA in ATCC Deposit No.: 75876;
   (f) a polypeptide fragment of the amino acid sequence as set forth in SEQ ID NO:4, wherein said fragment has enzymatic activity;
   (g) a polypeptide fragment of the amino acid sequence as set forth in SEQ ID NO:4, wherein said fragment contains conservative amino acid residue substitutions, and further wherein said fragment has enzymatic activity;
   (h) a polypeptide fragment of the amino acid sequence encoded by the human cDNA in ATCC Deposit No: 75876, wherein said fragrant has enzymatic activity;
   (i) a polypeptide fragment of the amino acid sequence encoded by the human cDNA in ATCC Deposit No: 75876, wherein said fragment contains conservative amino acid residue substitutions, and further wherein said fragment has enzymatic activity;
   (j) an antigenic polypeptide fragment of the amino acid sequence as set forth in SEQ ID NO:4, wherein said fragment is recognized by an antibody which specifically binds Ubiquitin Conjugating Enzyme-8;
   (k) an antigenic polypeptide fragment of the amino acid sequence as set forth in SEQ ID NO:4, wherein said fragment contains conservative amino acid residue substitutions, and further wherein said fragment is recognized by an antibody which specifically binds Ubiquitin Conjugating Enzyme-8;
   (l) an antigenic polypeptide fragment of the amino acid sequence encoded by the human cDNA in ATCC Deposit No: 75876, wherein said fragment is recognized by an antibody which specifically binds Ubiquitin Conjugating Enzyme-8;
   (m) an antigenic polypeptide fragment of the amino acid sequence encoded by the human cDNA in ATCC Deposit No: 75876, wherein said fragment contains conservative amino acid residue substitutions, and further wherein said fragment is recognized by an antibody which specifically binds Ubiquitin Conjugating Enzyme-8;
   (n) a polypeptide having at least 30 contiguous amino acid residues of the amino acid sequence as set forth in SEQ ID NO:4; and
   (o) a polypeptide having at least 30 contiguous amino acid residues of the amino acid sequence encoded by the human CDNA in ATCC Deposit No: 75876.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. The isolated polypeptide of claim 1, wherein said polypeptide is (e).

7. The isolated polypeptide of claim 1, wherein said polypeptide is (f).

8. The isolated polypeptide of claim 1, wherein said polypeptide is (g).

9. The isolated polypeptide of claim 1, wherein said polypeptide is (h).

10. The isolated polypeptide of claim 1, wherein said polypeptide is (i).

11. The isolated polypeptide of claim 1, wherein said polypeptide is (j).

12. The isolated polypeptide of claim 1, wherein said polypeptide is (k).

13. The isolated polypeptide of claim 1, wherein said polypeptide is (l).

14. The isolated polypeptide of claim 1, wherein said polypeptide is (m).

15. The isolated polypeptide of claim 1, wherein said polypeptide is (n).

16. The isolated polypeptide of claim 1, wherein said polypeptide is (o).

17. The isolated polypeptide of claim 2, wherein said polypeptide is further fused to a heterologous polypeptide.

18. The isolated polypeptide of claim 3, wherein said polypeptide is further fused to a heterologous polypeptide.

19. The isolated polypeptide of claim 4, wherein said polypeptide is further fused to a heterologous polypeptide.

20. The isolated polypeptide of claim 5, wherein said polypeptide is further fused to a heterologous polypeptide.

21. The isolated polypeptide of claim 6, wherein said polypeptide is further fused to a heterologous polypeptide.

22. The isolated polypeptide of claim 7, wherein said polypeptide is further fused to a heterologous polypeptide.

23. The isolated polypeptide of claim 8, wherein said polypeptide is further fused to a heterologous polypeptide.

24. The isolated polypeptide of claim 9, wherein said polypeptide is further fused to a heterologous polypeptide.

25. The isolated polypeptide of claim 10, wherein said polypeptide is further fused to a heterologous polypeptide.

26. The isolated polypeptide of claim 11, wherein said polypeptide is further fused to a heterologous polypeptide.

27. The isolated polypeptide of claim 12, wherein said polypeptide is further fused to a heterologous polypeptide.

28. The isolated polypeptide of claim 13, wherein said polypeptide is further fused to a heterologous polypeptide.

29. The isolated polypeptide of claim 14, wherein said polypeptide is further fused to a heterologous polypeptide.

30. The isolated polypeptide of claim 15, wherein said polypeptide is further fused to a heterologous polypeptide.

31. The isolated polypeptide of claim 16, wherein said polypeptide is further fused to a heterologous polypeptide.

32. The isolated polypeptide of claim 15, wherein said polypeptide has at least 50 contiguous amino acid residues of the amino acid sequence as set forth in SEQ ID NO:4.

33. The polypeptide of claim 16, wherein said polypeptide has at least 50 contiguous amino acid residues of the amino acid sequence encoded by the human cDNA in ATCC Deposit No. 75876.

34. An isolated polypeptide comprising a member selected from the group consisting of:
 (a) a polypeptide as set forth as amino acids 1 to 193 of SEQ ID NO:6;
 (b) a polypeptide as set forth as amino acids 2 to 193 of SEQ ID NO:6;
 (c) a polypeptide encoded by the human cDNA in ATCC Deposit No: 75878;
 (d) a polypeptide encoded by the human cDNA in ATCC Deposit No: 75878, except the N-terminal methionine;
 (e) a mature form of the polypeptide encoded by the human cDNA in ATCC Deposit No: 75878;
 (f) a polypeptide fragment of the amino acid sequence as set forth in SEQ ID NO:6,
 wherein said fragment has enzymatic activity;
 (g) a polypeptide fragment of the amino acid sequence as set forth in SEQ ID NO:6,
 wherein said fragment contains conservative amino acid residue substitutions, and further wherein said fragment has enzymatic activity;
 (h) a polypeptide fragment of the amino acid sequence encoded by the human cDNA in ATCC Deposit No: 75878, wherein said fragment has enzymatic activity;
 (i) a polypeptide fragment of the amino acid sequence encoded by the human cDNA in ATCC Deposit No: 75878, wherein said fragment contains conservative amino acid residue substitutions, and further wherein said fragment has enzymatic activity;
 (j) a polypeptide having an antigenic fragment of the amino acid sequence as set forth in SEQ ID NO:6, wherein said fragment is recognized by an antibody which specifically binds Ubiquitin Conjugating Enzyme-9;
 (k) a polypeptide having an antigenic fragment of the amino acid sequence as set forth in SEQ ID NO:6, wherein said fragment contains conservative amino acid residue substitutions, and further wherein said fragment is recognized by an antibody which specifically binds Ubiquitin Conjugating Enzyme-9;
 (l) an antigenic polypeptide fragment of the amino acid sequence encoded by the human cDNA in ATCC Deposit No: 75878, wherein said fragment is recognized by an antibody which specifically binds Ubiquitin Conjugating Enzyme-9;
 (m) an antigenic polypeptide fragment of the amino acid sequence encoded by the human cDNA in ATCC Deposit No: 75878, wherein said fragment contains conservative amino acid residue substitutions, and further wherein said fragment is recognized by an antibody which specifically binds Ubiquitin Conjugating Enzyme-9;
 (n) a polypeptide having at least 30 contiguous amino acid residues of the amino acid sequence as set forth in SEQ ID NO:6; and
 (o) a polypeptide having at least 30 contiguous amino acid residues of the amino acid sequence encoded by the human cDNA in ATCC Deposit No: 75878.

35. The isolated polypeptide of claim 34, wherein said polypeptide is (a).

36. The isolated polypeptide of claim 34, wherein said polypeptide is (b).

37. The isolated polypeptide of claim 34, wherein said polypeptide is (c).

38. The isolated polypeptide of claim 34, wherein said polypeptide is (d).

39. The isolated polypeptide of claim 34, wherein said polypeptide is (e).

40. The isolated polypeptide of claim 34, wherein said polypeptide is (f).

41. The isolated polypeptide of claim 34, wherein said polypeptide is (g).

42. The isolated polypeptide of claim 34, wherein said polypeptide is (h).

43. The isolated polypeptide of claim 34, wherein said polypeptide is (i).

44. The isolated polypeptide of claim 34, wherein said polypeptide is (j).

45. The isolated polypeptide of claim 34, wherein said polypeptide is (k).

46. The isolated polypeptide of claim 34, wherein said polypeptide is (l).

47. The isolated polypeptide of claim 34, wherein said polypeptide is (m).

48. The isolated polypeptide of claim 34, wherein said polypeptide is (n).

49. The isolated polypeptide of claim 34, wherein said polypeptide is (o).

50. The isolated polypeptide of claim 35, wherein said polypeptide is further fused to a heterologous polypeptide.

51. The isolated polypeptide of claim 36, wherein said polypeptide is further fused to a heterologous polypeptide.

52. The isolated polypeptide of claim 37, wherein said polypeptide is further fused to a heterologous polypeptide.

53. The isolated polypeptide of claim 38, wherein said polypeptide is further fused to a heterologous polypeptide.

54. The isolated polypeptide of claim 39, wherein said polypeptide is further fused to a heterologous polypeptide.

55. The isolated polypeptide of claim 40, wherein said polypeptide is further fused to a heterologous polypeptide.

56. The isolated polypeptide of claim 41, wherein said polypeptide is further fused to a heterologous polypeptide.

57. The isolated polypeptide of claim 42, wherein said polypeptide is further fused to a heterologous polypeptide.

58. The isolated polypeptide of claim 43, wherein said polypeptide is further fused to a heterologous polypeptide.

59. The isolated polypeptide of claim 44, wherein said polypeptide is further fused to a heterologous polypeptide.

60. The isolated polypeptide of claim 45, wherein said polypeptide is further fused to a heterologous polypeptide.

61. The isolated polypeptide of claim 46, wherein said polypeptide is further fused to a heterologous polypeptide.

62. The isolated polypeptide of claim 47, wherein said polypeptide is further fused to a heterologous polypeptide.

63. The isolated polypeptide of claim 48, wherein said polypeptide is further fused to a heterologous polypeptide.

64. The isolated polypeptide of claim 49, wherein said polypeptide is further fused to a heterologous polypeptide.

65. The isolated polypeptide of claim 48, wherein said polypeptide has at least 50 contiguous amino acid residues of the amino acid sequence as set forth in SEQ ID NO:6.

66. The isolated polypeptide of claim 49, wherein said polypeptide has at least 50 contiguous amino acid residues of the amino acid sequence encoded by the human cDNA in ATCC Deposit No: 75878.

* * * * *

SEQUENCE LISTING (1) GENERAL INFORMATION:

(iii) NUMBER OF SEQUENCES:  24

(2) INFORMATION FOR SEQ ID NO:1:

(i) SEQUENCE CHARACTERISTICS:
        (A) LENGTH:  444 BASE PAIRS
        (B) TYPE:  NUCLEIC ACID
        (C) STRANDEDNESS:  SINGLE
        (D) TOPOLOGY:  LINEAR (ii) MOLECULE TYPE:  cDNA (xi) SEQUENCE DESCRIPTION:  SEQ ID NO:1:

```
ATGGCTCTGA AGAGAATCCA CAAGGAATTG AATGATCTGG CACGGGACCC TCCAGCACAG      60

TGTTCAGCAG GTCCTGTTGG AGATGATATG TTCCATTGGC AAGCTACAAT AATGGGGCCA     120

AATGACAGTC CCTATCAGGG TGGAGTATTT TTCTTGACAA TTCATTTCCC AACAGATTAC     180

CTCTTCAAAC CACCTAAGGT TGCATTTACA ACAAGAATTT ATCATCCAAA TATTAACAGT     240

AATGGCAGCA TGTGTCTTGA TATTCTACGA TCACAGTGGT CTCCAGCACT AACTATTTCA     300

AAAGTACTCT TGTCCATCTG TTCTCTGTTG TGTGATCCCA ATCCAGATGA TCCTTTAGTG     360

CCTGAGATTG CTCGGATCTA CAAAACAGAT AGAGAAAAGT ACAACAGAAT AGCTCGGGAA     420

TGGACTCAGA AGTATGCGAT GTAA                                           444
```

(2) INFORMATION FOR SEQ ID NO:2:

(i) SEQUENCE CHARACTERISTICS:
        (A) LENGTH:  147 AMINO ACIDS
        (B) TYPE:  AMINO ACID
        (C) STRANDEDNESS:
        (D) TOPOLOGY:  LINEAR (ii) MOLECULE TYPE:  PROTEIN (xi) SEQUENCE DESCRIPTION:  SEQ ID NO:2:

```
Met Ala Leu Lys Arg Ile His Lys Glu Leu Asn Asp Leu Ala Arg
                 5                  10                  15

Asp Pro Pro Ala Gln Cys Ser Ala Gly Pro Val Gly Asp Asp Met
                20                  25                  30

Phe His Trp Gln Ala Thr Ile Met Gly Pro Asn Asp Ser Pro Tyr
                35                  40                  45

Gln Gly Gly Val Phe Phe Leu Thr Ile His Phe Pro Thr Asp Tyr
                50                  55                  60

Leu Phe Lys Pro Pro Lys Val Ala Phe Thr Thr Arg Ile Tyr His
                65                  70                  75

Pro Asn Ile Asn Ser Asn Gly Ser Met Cys Leu Asp Ile Leu Arg
                80                  85                  90

Ser Gln Trp Ser Pro Ala Leu Thr Ile Ser Lys Val Ile Leu Ser
```

```
                 95                  100                 105
Ile Cys Ser Leu Leu Cys Asp Pro Asn Pro Asp Asp Pro Leu Val
                110                 115                 120

Pro Glu Ile Ala Arg Ile Tyr Lys Thr Asp Arg Glu Lys Tyr Asn
                125                 130                 135

Arg Ile Ala Arg Glu Trp Thr Gln Lys Tyr Ala Met
                140                 145
```

(2) INFORMATION FOR SEQ ID NO:3:

(i) SEQUENCE CHARACTERISTICS:
        (A) LENGTH: 465 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:3:

```
ATGGCGGCCA GCAGGAGGCT GATGAAGGAG CTTGAAGAAA TCCGCAAATG TGGGATGAAA    60

AACTTCCGTA ACATCCAGGT TGATGAAGCT AATTTATTGA CTTGGCAAGG GCTTATTGTT   120

CCTGACAACC CTCCATATGA TAAGGGAGCC TTCAGAATCG AAATCAACTT TCCAGCAGAG   180

TACCCATTCA AACCACCGAA GATCACATTT AAAACAAAGA TCTATCACCC AAACATCGAC   240

GAAAAGGGGC AGGTCTGTCT GCCAGTAATT AGTGCCGAAA ACTGGAAGCC AGCAACCAAA   300

ACCGACCAAG TAATCCAGTC CCTCATAGCA CTGGTGAATG ACCCCAGCC TGAGCACCCG    360

CTTCGGGCTG ACCTAGCTGA AGAATACTCT AAGGACCGTA AAAAATTCTG TAAGAATGCT   420

GAAGAGTTTA CAAAGAAATA TGGGGAAAAG CGACCTGTGG ACTAA                   465
```

(2) INFORMATION FOR SEQ ID NO:4:

(i) SEQUENCE CHARACTERISTICS:
        (A) LENGTH: 154 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:4:

```
Met Ala Ala Ser Arg Arg Leu Met Lys Glu Leu Glu Glu Ile Arg
                  5                  10                  15

Lys Cys Gly His Lys Asn Phe Arg Asn Ile Gln Val Asp Glu Ala
                 20                  25                  30

Asn Leu Leu Thr Trp Gln Gly Leu Ile Val Pro Asp Asn Pro Pro
                 35                  40                  45

Tyr Asp Lys Gly Ala Phe Arg Ile Glu Ile Asn Phe Pro Ala Glu
                 50                  55                  60

Tyr Pro Phe Lys Pro Pro Lys Ile Thr Phe Lys Thr Lys Ile Tyr
                 65                  70                  75

His Pro Asn Ile Asp Glu Lys Gly Gln Val Cys Leu Pro Val Ile
                 80                  85                  90

Ser Ala Glu Asn Trp Lys Pro Ala Thr Lys Thr Asp Gln Val Ile
                 95                 100                 105

Gln Ser Leu Ile Ala Leu Val Asn Asp Pro Gln Pro Glu His Pro
                110                 115                 120

Leu Arg Ala Asp Leu Ala Glu Glu Tyr Ser Lys Asp Arg Lys Lys
                125                 130                 135
```

Phe Cys Lys Asn Ala Glu Glu Phe Thr Lys Lys Tyr Gly Glu Lys
            140                 145                 150

Arg Pro Val Asp (2) INFORMATION FOR SEQ ID NO:5:

(i) SEQUENCE CHARACTERISTICS:
        (A) LENGTH: 582 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:5:

```
ATGACAGTCC AAGCACTAGG GCACGAGAGT TCCGATGGAG ATCAACGTGA AAGTGTTCAG      60

CAAGAACCAG AAAGAGAACA AGTTCAGCCC AAGAAAAAGG AGGGAAAAAT ATCCAGCAAA     120

ACCGCTGCTA AATTGTCAAC TAGTGCTAAA AGAATTCAGA AGGAACTTGC AGAAATCACA     180

TTGGACCCTC CTCCCAACTG TAGTGCTGGA CCCAAAGGAG ACAACATTTA TGAATGGAGG     240

TCAACTATAT TGGGACCCCC AGGATCTGTC TATGAAGGAG GGGTGTTCTT TCTTGACATT     300

ACCTTTTCAC CAGACTATCC GTTTAAACCC CCTAAGGTTA CCTTCCGAAC AAGATTTTTT     360

CAGTGTAATA TTAACAGCCA AGGTGTGATC TGTCTGGACA TCTTAAAGGA CAACTGGAGT     420

CCGGCTTTAA CTATTTCTAA AGTTCTCCTC TCCATCTGCT CACTTCTTAC AGATTGCAAC     480

CCTGCTGACC CTCTGGTGGG GAGCATCGCC ACACAGTACA TGACCAACAG AGGAGAGCAT     540

GACCGGATGG ACAGACAGTG GACCAAGCGG TACGCCACAT AG                       582
```

(2) INFORMATION FOR SEQ ID NO:6:

(i) SEQUENCE CHARACTERISTICS:
        (A) LENGTH: 193 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:6:

Met Thr Val Gln Ala Leu Gly His Glu Ser Ser Asp Gly Asp Gln
                 5                  10                  15

Arg Glu Ser Val Gln Gln Glu Pro Glu Arg Glu Gln Val Gln Pro
                20                  25                  30

Lys Lys Lys Glu Gly Lys Ile Ser Ser Lys Thr Ala Ala Lys Leu
                35                  40                  45

Ser Thr Ser Ala Lys Arg Ile Gln Lys Glu Leu Ala Glu Ile Thr
                50                  55                  60

Leu Asp Pro Pro Asn Cys Ser Ala Gly Pro Lys Gly Asp Asn
                65                  70                  75

Ile Tyr Glu Trp Arg Ser Thr Ile Leu Gly Pro Pro Gly Ser Val
                80                  85                  90

Tyr Glu Gly Gly Val Phe Phe Leu Asp Ile Thr Phe Ser Pro Asp
                95                 100                 105

Tyr Pro Phe Lys Pro Pro Lys Val Thr Phe Arg Thr Arg Phe Phe
               110                 115                 120

His Cys Asn Ile Asn Ser Gln Gly Val Ile Cys Leu Asp Ile Leu
               125                 130                 135

Lys Asp Trp Trp Ser Pro Ala Leu Thr Ile Ser Lys Val Leu Leu
               140                 145                 150

Ser Ile Cys Ser Leu Leu Thr Asp Cys Asn Pro Ala Asp Pro Leu
            155                 160                 165

Val Gly Ser Ile Ala Thr Cys Tyr Met Thr Asn Arg Gly Glu His
        170                 175                 180

Asp Arg Met Asp Arg Gln Trp Thr Lys Arg Tyr Ala Thr
                185                 190

(2) INFORMATION FOR SEQ ID NO:7:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:7:

CCCGGATCCG CTTCGAAGAG AATCCACAAG                     30

(2) INFORMATION FOR SEQ ID NO:8:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:8:

GCGCAAGCTT TTACATCGCA TACTTCTGAG TCC                  33

(2) INFORMATION FOR SEQ ID NO:9:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:9:

CCCGGATCCG CGGCCAGCAG GAGGCTGATG                     30

(2) INFORMATION FOR SEQ ID NO:10:

(i) SEQUENCE CHARACTERISTICS:
        (A) LENGTH: 25 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:10:

GCGCAAGCTT TTAGTCCACA GGTCG                          25

(2) INFORMATION FOR SEQ ID NO:11:

(i) SEQUENCE CHARACTERISTICS:
        (A) LENGTH: 29 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:11:

GCGCGGATCC ACAGTCCAAG CACTAGGGC                29

(2) INFORMATION FOR SEQ ID NO:12:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:12:

GCGCAAGCTT CTATGTGGCG TACCGCTTGG              30

(2) INFORMATION FOR SEQ ID NO:13:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:13:

GCGCGGATCC ACCATGGCTC TGAAGAGAAT CC           32

(2) INFORMATION FOR SEQ ID NO:14:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:14:

GCGCTCTAGA TTACATCGCA TACTTCTGAG TCC          33

(2) INFORMATION FOR SEQ ID NO:15:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:15:

GCGCGGATCC ACCATGGCGG CCAGCAGGAG GCT          33

(2) INFORMATION FOR SEQ ID NO:16:

(i) SEQUENCE CHARACTERISTICS:
        (A) LENGTH: 25 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:16:

GCGCTCTAGA TTAGTCCACA GGTCG                   25

(2) INFORMATION FOR SEQ ID NO:17:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:17:

GATCGGATCC ACCATGACAG TCCAAGCACT AG                                    32

(2) INFORMATION FOR SEQ ID NO:18:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:18:

GCGCTCTAGA CTATGTGGCG TACCGCTTGG                                       30

(2) INFORMATION FOR SEQ ID NO:19:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:19:

GCGCGGATCC ACCATGGCTC TGAAGAGAAT CC                                    32

(2) INFORMATION FOR SEQ ID NO:20:

(i) SEQUENCE CHARACTERISTICS:
        (A) LENGTH: 57 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:20:

GCGCTCTAGA TCAAGCGTAG TCTGGGACGT CGTATGGGTA CATCGCATAC TTCTGAG         57

(2) INFORMATION FOR SEQ ID NO:21:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:21:

GCGCGGATCC ACCATGGCGG CCAGCAGGAG GC                                    32

(2) INFORMATION FOR SEQ ID NO:22:

(i) SEQUENCE CHARACTERISTICS:
        (A) LENGTH: 52 BASE PAIRS (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:22:

GCGCTCTAGA TCAAGCGTAG TCTGGGACGT CGTATGGGTA GTCCACAGGT CG           52

(2) INFORMATION FOR SEQ ID NO:23:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:23:

GATCGGATCC ACCATGACAG TCCAAGCACT AG                                  32

(2) INFORMATION FOR SEQ ID NO:24:

(i) SEQUENCE CHARACTERISTICS:
        (A) LENGTH: 57 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:24:

GCGCTCTAGA TCAAGCGTAG TCTGGGACGT CGTATGGGTA TGTGGCGTAC CGCTTGG      57